(12) United States Patent
Jemelka et al.

(10) Patent No.: US 12,010,766 B2
(45) Date of Patent: Jun. 11, 2024

(54) WINDOW HEATING APPARATUS

(71) Applicant: Honeywell International Inc., Morris Plains, NJ (US)

(72) Inventors: Ondrej Jemelka, Kokory (CZ); Jan Adamek, Brno (CZ); Radek Stupka, Brno (CZ); Marek Fikera, Brno (CZ)

(73) Assignee: Honeywell International Inc., Morris Plains, NJ (US)

( * ) Notice: Subject to any disclaimer, the term of this patent is extended or adjusted under 35 U.S.C. 154(b) by 935 days.

(21) Appl. No.: 16/692,706

(22) Filed: Nov. 22, 2019

(65) Prior Publication Data

US 2021/0160969 A1   May 27, 2021

(51) Int. Cl.
| | |
|---|---|
| *H05B 3/84* | (2006.01) |
| *G01N 21/03* | (2006.01) |
| *G01N 21/3504* | (2014.01) |
| *G01N 33/00* | (2006.01) |
| *G02B 7/02* | (2021.01) |
| *G02B 27/00* | (2006.01) |
| *H05B 3/26* | (2006.01) |

(52) U.S. Cl.
CPC ........... *H05B 3/84* (2013.01); *G01N 21/0332* (2013.01); *G01N 21/3504* (2013.01); *G01N 33/0029* (2013.01); *G02B 7/028* (2013.01); *G02B 27/0006* (2013.01); *H05B 3/26* (2013.01); *H05B 2214/02* (2013.01)

(58) Field of Classification Search
CPC ........ H05B 3/84; H05B 3/26; H05B 2214/02; G01N 33/0029; G01N 21/0332; G01N 21/3504; G02B 7/028; G02B 27/0006
See application file for complete search history.

(56) References Cited

U.S. PATENT DOCUMENTS

| | | | |
|---|---|---|---|
| 5,146,092 A | 9/1992 | Apperson et al. | |
| 7,301,125 B2* | 11/2007 | Davis .................... | A61B 5/083 73/23.3 |
| 7,749,446 B2 | 7/2010 | Peterman | |

(Continued)

FOREIGN PATENT DOCUMENTS

| | | |
|---|---|---|
| EP | 2169384 A1 | 3/2010 |
| EP | 3352008 A1 | 7/2018 |

(Continued)

OTHER PUBLICATIONS https://learn.sparkfun.com/tutorials/pcb-basics/all (Year: 2019).*

(Continued)

*Primary Examiner* — Elizabeth M Kerr
(74) *Attorney, Agent, or Firm* — Alston & Bird LLP

(57) ABSTRACT

Various example embodiments described herein relate to a window heating apparatus. The window heating apparatus comprises a frame, a heater assembly disposed on the frame, and a glass window. The heater assembly comprises a base having a first side and a second side and defines a first opening. The heater assembly comprises a Printed Circuit Board (PCB) laminated on the first side of the base along an inner edge of the base. The PCB defines a second opening, wherein the first opening and the second opening are aligned coaxially. The glass window is disposed on the base and the second side of the base is in direct contact with the glass window.

13 Claims, 8 Drawing Sheets

(56) References Cited

U.S. PATENT DOCUMENTS 11,178,316 B2 * 11/2021 Tagaya .................... G03B 17/55
2009/0231588 A1      9/2009 Sutton et al.
2020/0353561 A1 * 11/2020 Thiel .................... B23K 26/064

FOREIGN PATENT DOCUMENTS

| KR | 2011-0068442 A |   | 6/2011 |
| KR |  20110068442 A | * | 6/2011 |
| KR | 2012-0097868 A |   | 9/2012 |

OTHER PUBLICATIONS

Translation of KR-20110068442-A (Year: 2011).*
Extended European Search Report issued in European Application No. 20207056.1 dated Apr. 28, 2021, 9 pages.
Intention to grant dated Sep. 26, 2023 for EP Application No. 20207056, 9 page(s).
Decision to grant a European patent dated Jan. 25, 2024 for EP Application No. 20207056, 2 page(s).

* cited by examiner

WINDOW HEATING APPARATUS

TECHNOLOGICAL FIELD

The present disclosure relates generally to a heater assembly and a system and apparatus associated therewith. More particularly, the invention pertains to such heating apparatus which are adapted to remove condensed water or snow from a glass window of a gas detector.

BACKGROUND

It is a common safety practice to use two detectors with a means of selecting different wavelength bands of a source light. For example, a reference signal can be used in conjunction with a sample signal to determine any drop in the intensity of the radiation output, any loss of intensity due to fouling of the detector (e.g., a fogged or dirty window, etc.), or any substances in the light path that may affect the intensity of the radiation (e.g., dust, water vapor, etc.). In radiation-based gas detectors, snow or water condensation on a glass window of the gas detectors affect transparency of the glass window through which radiation reaches the gas detectors.

SUMMARY

In accordance with various embodiments of the present disclosure, a window heating apparatus may be provided for heating a glass window of a gas detector and removing snow or condensed water from the glass window. The window heating apparatus comprises a frame, and a heater assembly disposed on the frame. The heater assembly comprises a base having a first side and a second side, wherein the second side is positioned on the opposite side of the first side. The base defines a first opening about a center axis of the base. The heater assembly further comprises a Printed Circuit Board (PCB) laminated on the first side of the base along an inner edge of the base. The PCB has one or more heating elements for heating the glass window. The PCB defines a second opening about a center axis of the PCB. The base and the PCB are coupled such that the first opening and the second opening are aligned coaxially with each other. The window heating apparatus further comprises a glass window disposed on the second side of the base such that the glass window is in direct contact with the base on the second side.

Further, in another exemplary embodiment, an apparatus for detecting gas based on radiations is disclosed. The apparatus comprises a frame, and a heater assembly disposed on the frame. The heater assembly comprises a base defining a first opening about a center axis of the base and a PCB. The PCB is laminated on the base of the heater assembly, the PCB having one or more heating elements and defining a second opening about a center axis of the PCB. In an example, the second opening has the same diameter as the first opening. Further, the apparatus comprises a glass window disposed on the heater assembly, wherein the glass window is in direct contact with the base of the heater assembly. The apparatus further comprises a front cover configured to secure with the frame, the front cover encasing the glass window and the heater assembly when the front cover is secured to the frame.

Further, in another exemplary embodiment, a heater assembly configured to couple to a glass window of a gas detector is disclosed. The heater assembly comprises a base having a first side and a second side, wherein the second side is positioned opposite to the first side. The base is circular in shape and has a first opening defined about a center axis of the base. The heater assembly further comprises a PCB laminated on the first side of the base along an inner circumference of the base. The PCB has one or more heating elements and has a second opening defined about a center axis of the PCB, wherein the first opening and the second opening are aligned coaxially. The second side of the base is configured to be coupled to the glass window, and an area of each of the one or more heating elements is based on a diameter of the glass window.

BRIEF DESCRIPTION OF THE DRAWINGS

The description of the illustrative embodiments can be read in conjunction with the accompanying figures. It will be appreciated that for simplicity and clarity of illustration, elements illustrated in the figures have not necessarily been drawn to scale. For example, the dimensions of some of the elements are exaggerated relative to other elements. Embodiments incorporating teachings of the present disclosure are shown and described with respect to the figures presented herein, in which.

DETAILED DESCRIPTION

Figure 1A:
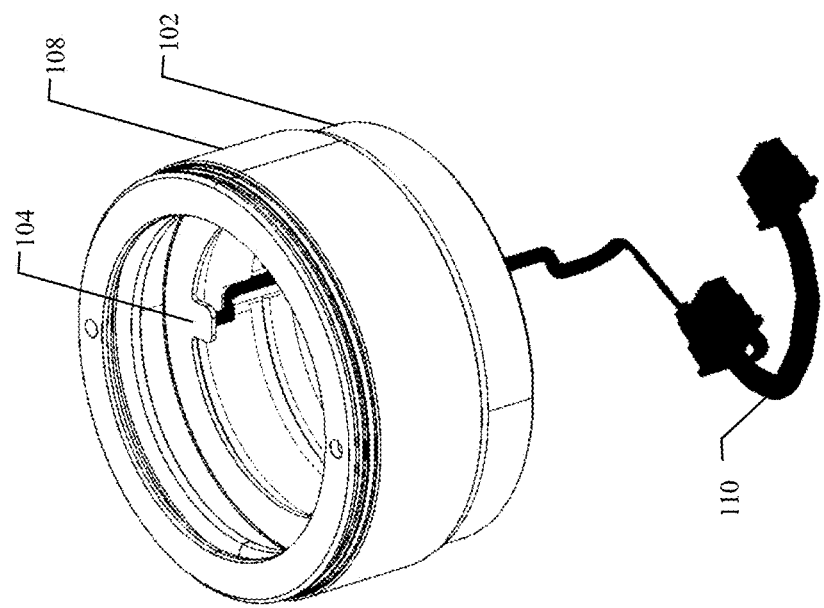
FIG. 1A illustrates an isometric view of a window heating apparatus, according to one or more embodiments described herein.

Some embodiments of the present disclosure will now be described more fully hereinafter with reference to the accompanying drawings, in which some, but not all embodiments of the disclosure are shown. Indeed, these disclosures may be embodied in many different forms and should not be construed as limited to the embodiments set forth herein; rather, these embodiments are provided so that this disclosure will satisfy applicable legal requirements. Like numbers refer to like elements throughout. Terminology used in this patent is not meant to be limiting insofar as devices described herein, or portions thereof, may be attached or utilized in other orientations.

The phrases "in one embodiment," "according to one embodiment," "in some embodiments," and the like generally mean that the particular feature, structure, or characteristic following the phrase may be included in at least one embodiment of the present disclosure, and may be included in more than one embodiment of the present disclosure (importantly, such phrases do not necessarily refer to the same embodiment).

The word "exemplary" is used herein to mean "serving as an example, instance, or illustration." Any implementation described herein as "exemplary" is not necessarily to be construed as preferred or advantageous over other implementations.

If the specification states a component or feature "may," "can," "could," "should," "would," "preferably," "possibly," "typically," "optionally," "for example," "often," or "might" (or other such language) be included or have a characteristic, that particular component or feature is not required to be included or to have the characteristic. Such component or feature may be optionally included in some embodiments, or it may be excluded.

The "frame" as described herein may correspond to an outer structure include a ridge to receive a heater assembly. The frame may be placed proximally to an end of a transmitter or a receiver of a radiation-based gas detector through which radiations are received. Further, the frame according to the present invention can be designed as a module or an attachable sensor cartridge to cover and protect internal components of the gas detector. In addition, shape and configuration of the frame can be selected based on the type and shape of the gas detector.

The "Printed Circuit Board" (PCB) as described herein may comprise a circuitry which can be coupled to a base of a heater assembly of the gas detector. The circuitry of the PCB may comprise one or more heating elements to produce heat. Further, in one exemplary embodiment, the PCB has the same shape as the frame and the base of the heater assembly.

Usually, radiation-based gas detectors, during extreme ambient temperatures and humidity conditions, have snow or moisture collected on glass windows of the gas detectors through which the gas detectors receive radiations for detection. The snow and condensed water present on a glass window affects transparency of the glass window thereby affecting the amount of radiations received through the glass window. This deteriorates performance of a gas detector. Generally, heating elements are attached to the glass window using glue or a mechanical structure to mount the heating elements on the glass window. The glue layer on the glass window blocks a portion of the glass window thereby affecting the transparency, and the mechanical structures are complex to install and operate.

The apparatuses described herein disclose a window heating apparatus that may heat the glass window of the gas detector. The window heating apparatus comprises a frame, a heater assembly, and a glass window. In an example, the heater assembly is disposed on the frame along a ridge of the frame. The ridge is defined along an inner surface of the frame. The glass window is disposed on the heater assembly and a front cover is placed on the frame. The front cover is coupled to the frame such that the front cover and the frame collectively encase the heater assembly and the glass window.

In an example embodiment, the heater assembly comprises a base and a Printed Circuit Board (PCB). The base of the heater assembly comprises a first side and a second side disposed on opposite sides of the heater assembly. The base also defines a first opening about a center axis of the base. The PCB is laminated on the first side of the base along an inner edge of the base and defines a second opening. The second opening is disposed about a center axis of the PCB. The PCB is coupled to the base in a manner such that the first opening and the second opening are coaxially aligned. In an assembled state, when the front cover is coupled to the frame, the heater assembly is coupled to the glass window on the second side.

The window heating apparatus as described herein can efficiently heat the glass window of the gas detector and remove snow and condensed water from the glass window. The window heating apparatus has the heater assembly placed between the frame and the glass window therefore avoiding the need to glue the heater assembly to the glass window. The window heating apparatus heats the glass window by first heating the base of the heater assembly, from where the heat is transferred to the glass window in a homogenous manner, thereby preventing direct contact of heating elements with the glass window and avoiding localized overheating and damage to a glass surface.

The details regarding additional components and functioning of various components of the window heating apparatus are explained further with respect to description of forthcoming figures.

Figure 1B:
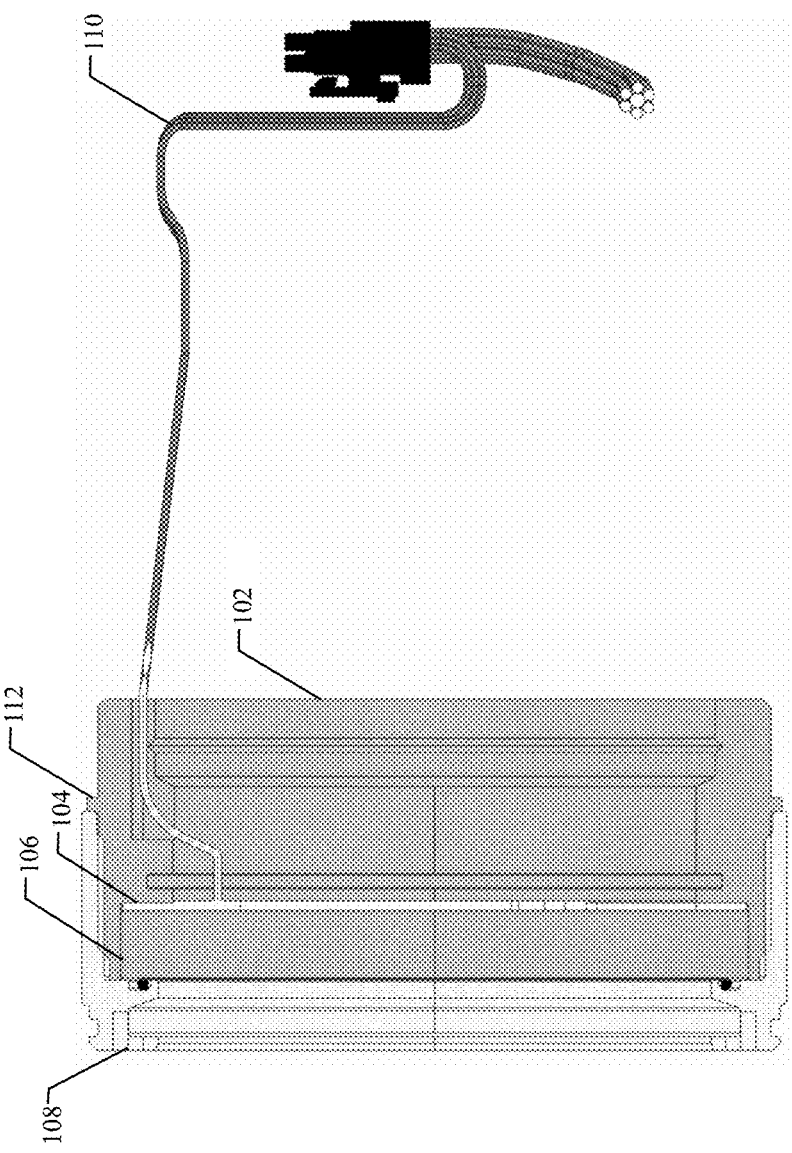
FIG. 1B illustrates a side view of a window heating apparatus, according to one or more embodiments described herein.

FIGS. 1A and 1B illustrate an isometric view and a side view of a window heating apparatus 100 respectively, in accordance with one or more example embodiments described herein. The window heating apparatus 100 may be placed in a transmitter or a receiver of a radiation-based gas detector in proximity to an end through which radiations are received. In one exemplary embodiment, the window heating apparatus 100 includes a frame 102, a heater assembly 104, a glass window 106 and a front cover 108. The window heating apparatus 100 comprises a power cord 110 connected to the heater assembly 104. In an example, the heater assembly 104 is disposed on a ridge of the frame 102. The ridge may be defined along an inner surface of the frame 102 and has a same shape as the frame 102. The front cover 108 is secured to the frame 102 such that a first end of the front cover 108 is placed on an extended portion 112 of the frame 102. The extended portion 112 is disposed along an outer surface of the frame 102.

In an example, the front cover 108 may be press fit onto the frame 102. In another example, a portion of the frame 102 may be threaded to secure the front cover 108 to the frame 102. The front cover 108 is coupled to the frame 102 such that the front cover 108 and the frame 102 completely encase the heater assembly 104 and the glass window 106. In an assembled state, the window heating apparatus 100 allows for radiations to pass through the window heating apparatus 100 with reduced blocking at the glass window 106. In an example, the window heating apparatus 100 comprises a temperature sensor to measure temperature of the glass window 106. The temperature sensor periodically measures the temperature of the glass window 106 after a preset time and sends a signal for powering off the window heating apparatus 100 when the temperature of the glass window 106 reaches 50° C.

Figure 2:
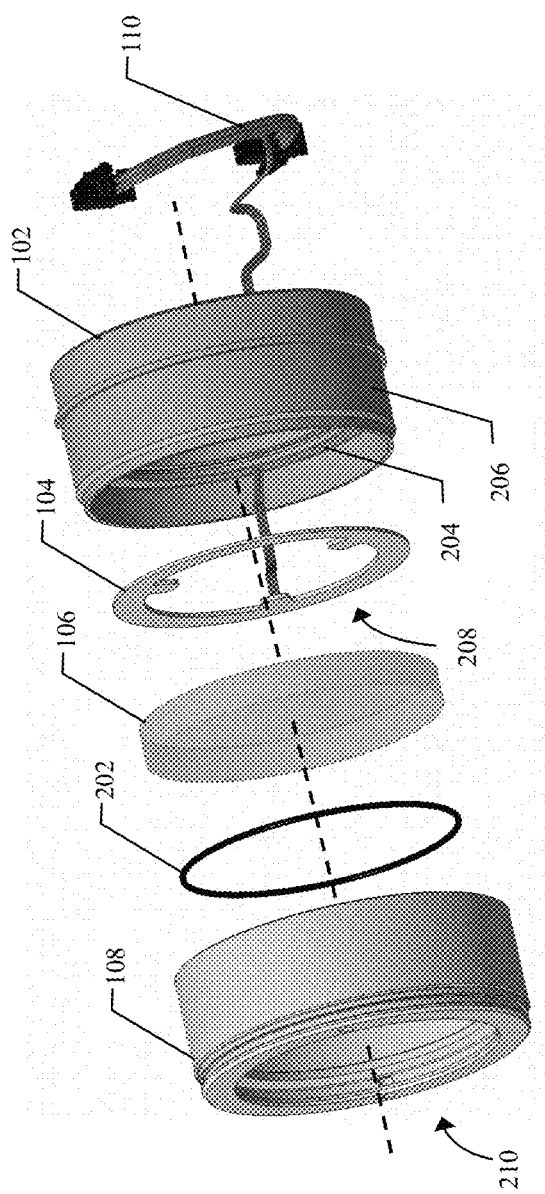
FIG. 2 illustrates an exploded view of a window heating apparatus, according to one or more embodiments described herein.

FIG. 2 illustrates an exploded view of the window heating apparatus 100, according to one or more example embodiments described herein. The window heating apparatus 100 has the frame 102, the heater assembly 104, the glass window 106, the front cover 108 and the power cord 110. In addition, the window heating apparatus 100 has a gasket 202.

The frame 102 has a ridge 204 that is radially extended outwardly from an inner surface of the frame 102. The ridge 204 is configured to receive the heater assembly 104 during assembly of the window heating apparatus 100. Upon placing the heater assembly 104 on the ridge 204 of the frame 102, the heater assembly 104 is fitted within the frame 102 with minimum or no sideways and downward movement.

The glass window 106 is disposed on the heater assembly 104 on the ridge 204. The diameter of the glass window 106 is about 83.50 millimeters (mm). In an example, the gasket 202 is disposed on the glass window 106. The glass window 106, in the assembled state, presses the heater assembly 104 against the ridge 204 of the frame 102. In an example embodiment, a portion 206 of the frame 102 has external threads on an outer surface to engage with threads on an inner surface of the front cover 108 to secure the front cover 108 to the frame 102. Additionally, any other fastening means may be used to secure the front cover 108 to the frame 102. The heater assembly 104 has an opening 208 and the front cover 108 has an opening 210. In an example, the diameter of the opening 208 is same as the diameter of the opening 210. When the window heating apparatus 100 is in the assembled state, the opening 208 and the opening 210 align coaxially.

Figure 3:
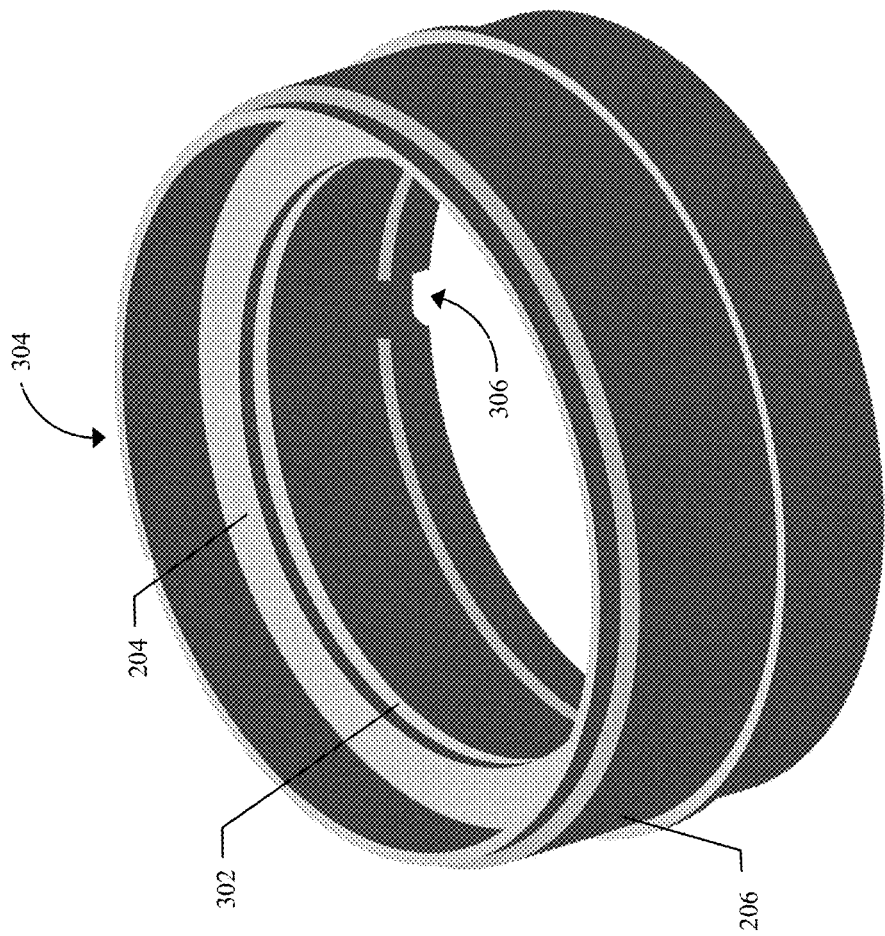
FIG. 3 illustrates an isometric view of a frame of the window heating apparatus, according to one or more embodiments described herein.

FIG. 3 illustrates an isometric view of the frame 102 of the window heating apparatus 100, according to one or more embodiments described herein. As shown in FIG. 3, the frame 102 has a circular shape that is based on a shape of the glass window 106 or the gas detector. In an example, the shape of the frame 102 may be one of a square, rectangular, or any other shape based on the shape of the glass window 106 or the gas detector.

The ridge 204 of the frame 102 is configured to receive the heater assembly 104. The width of the ridge 204 is either equal to or less than a width of the heater assembly 104. The frame 102 has a groove 302 of a predefined spacing beneath the ridge 204. The groove 302 is defined within an inner surface along an inner circumference of the frame 102. The groove 302 allows absorbing pressure to be applied to the glass window 106 during installation or assembly of the window heating apparatus 100 or during operation of the window heating apparatus 100. Any pressure applied may be absorbed by the groove 302 based on compression of the groove 302 within the spacing and any impact on the glass window 106 may be reduced.

The frame 102 has an opening 304 having a diameter equal or greater than a diameter of the heater assembly 104. The frame has a spacing 306 to allow passage of the power cord 110 through the frame 102.

Figure 4A:
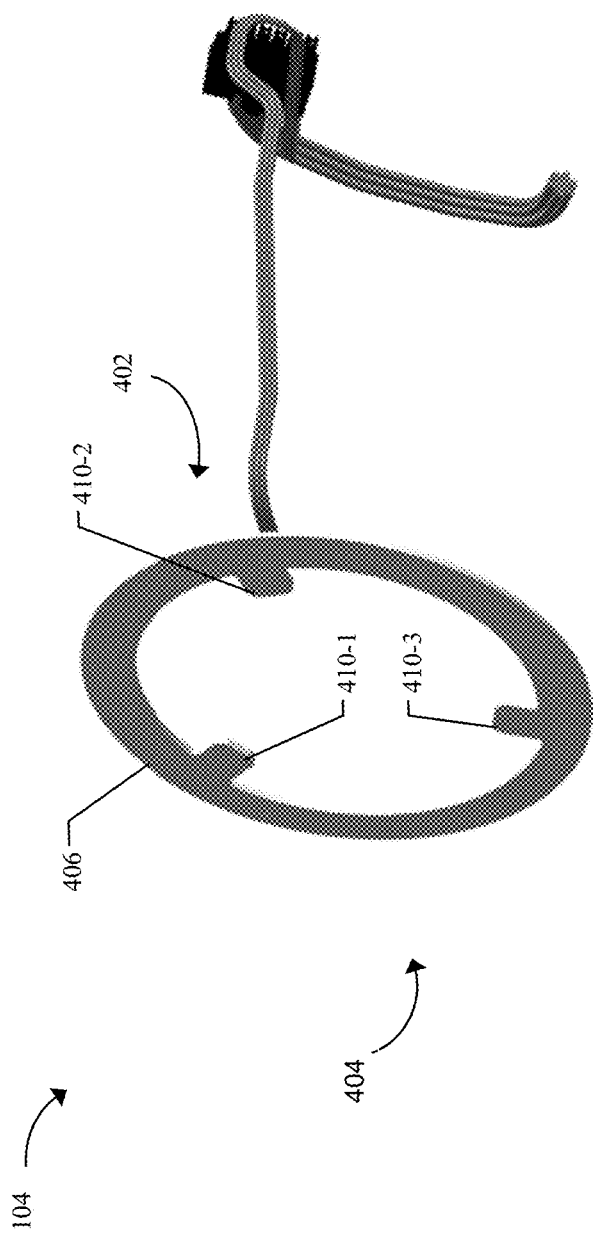
FIG. 4A illustrates an isometric view of a heater assembly of a window heating apparatus, according to one or more embodiments described herein.
Figure 4B:
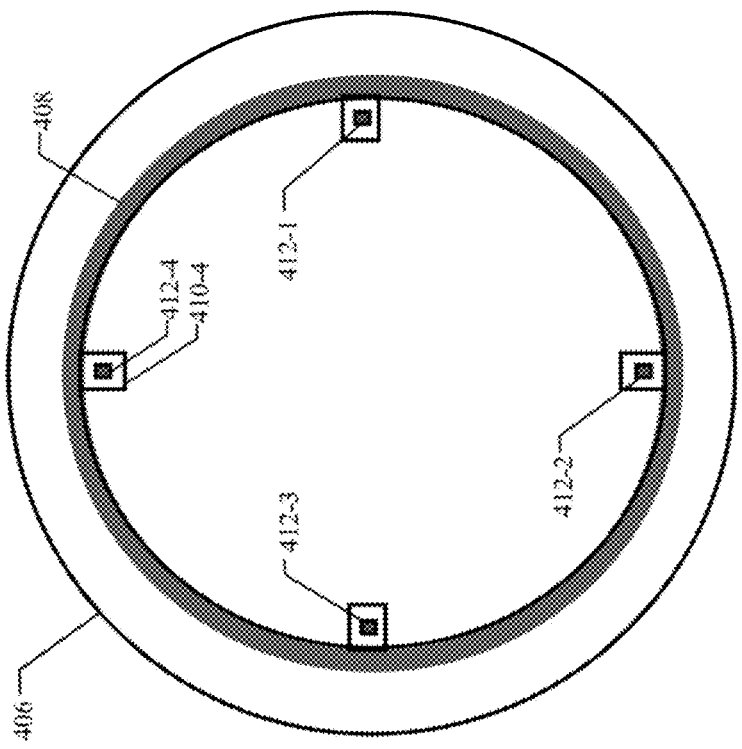
FIG. 4B illustrates a rear view of a heater assembly of a window heating apparatus, according to one or more embodiments described herein.
Figure 4B:

FIG. 4A illustrates a front view of the heater assembly 104, and FIG. 4B displays a rear view of the heater assembly 104, according to one or more embodiments described herein. The heater assembly 104 has a first side 402 and a second side 404. The first side 402 and the second side 404 are disposed on opposite sides of the heater assembly 104. The heater assembly 104 comprises a base 406 and a PCB 408. The base 406 is made of a metal, such as aluminum or milled copper and has a circular shape. The base 406 has a first opening about a center axis of the base 406.

The base 406 has one or more teeth 410-1, 410-2, 410-3 extending outwardly from the base 406, collectively referred to as tooth 410. In an example, a width of each of the one or more teeth 410 is about 8 mm and an area of a single tooth is about 56 mm². Distance between a distal end of each tooth from an inner circumference of the base 406 to the center of the base 406 is about 26 mm. In FIG. 4A, three teeth 410-1, 410-2, 410-3 are shown, and in FIG. 4B, a fourth tooth 410-4 is shown, however, depending upon heating required for the glass window 106, the number of teeth may vary. The PCB 408 is a metal-based PCB, for instance, aluminum based, and is coupled to the base 406 on the rear side or the first side 402 of the heater assembly 104. The PCB 408 has a second opening about a center axis of the PCB 408.

In an example embodiment, the PCB 408 includes heating elements 412-1, 412-2, 412-3, 412-4, collectively referred to as heating element 412, where each heating element 412 is disposed on the tooth 410. In an example, the heating elements 412-1, 412-2, 412-3 and 412-4 are arranged along an inner edge of the base 406. The number, size and area of the heating elements 412-1, 412-2, 412-3 and 412-4 may vary based on size and diameter of the glass window 106. For a smaller diameter of the glass window 106, requiring less heating, the number and area of heating elements 412-1, 412-2, 412-3, 412-4 may be less and for a glass window 106 of longer diameter, requiring a higher amount of heating, the area of the heating elements 412-1, 412-2, 412-3, 412-4 may be larger. In an example, an area of the PCB 408 is about 463 mm².

In an example, the heating elements 412-1, 412-2, 412-3 and 412-4 may include one or more resistors. In an example, an area of a single resistor is in the range of about 3.52 mm² to 5.5 mm². The flow of current through the resistor produces heat and the base 406, which is in contact with the heating members 412-1, 412-2, 412-3 and 412-4 is heated. The heat is then transferred from the base 406 to the glass window 106 to which the base 406 is in direct contact. The base 406 provides a conductive thermal exchange surface for the glass window 106 and facilitates distributed heating of the glass window 106, thereby preventing localized overheating. In one example, depending upon an amount of heating required, the number of resistors may be increased or decreased for each heating element 412. The heating elements 412-1, 412-2, 412-3 and 412-4 and the teeth 410-1, 410-2, 410-3, and 410-4 are arranged in such a manner that the glass window 106 is heated in a homogenous manner. Further, the base 406 is aligned along an outer circumference of the glass window 106 that is not used for receiving radiations, thereby not affecting optical efficiency of the gas detector.

The heater assembly 104 has an inner diameter of about 70 mm and after the PCB 408 is attached to the base 406, the inner diameter of the heater assembly 104 through which radiations are received is about 66 mm. In an example, a total area of the heater assembly 104 in contact with the glass window 106 is about 2091 mm².

Figure 5:
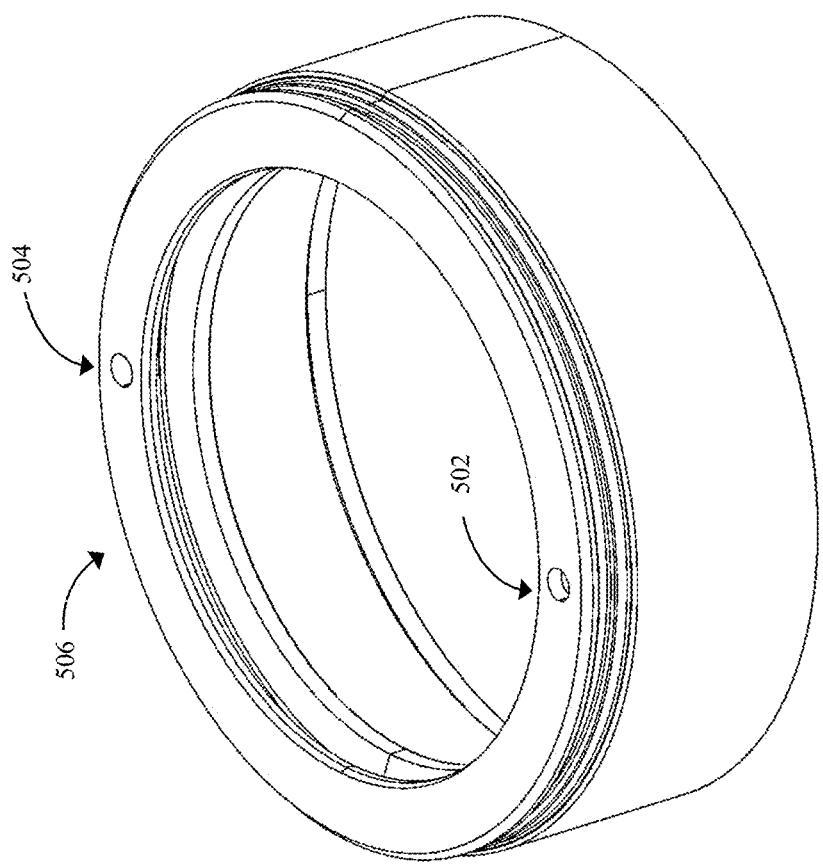
FIG. 5 depicts a perspective view of a front cover of a window heating apparatus, according to one or more embodiments described herein.

FIG. 5 illustrates the front cover 108, according to one or more embodiments described herein. The front cover 108, as shown, has a circular shape. The front cover 108 may have other shapes depending upon the shape of the gas detector or the glass window 106. The front cover 108 has two holes 502 and 504 on an upper surface of the front cover 108. The holes 502 and 504 may be used for inserting screws to couple the front cover 108 to the glass window 106 which is positioned beneath the front cover 108 and to tightly hold the glass window 106 against the frame 102. Further, the front cover 108 can be coupled with the frame 102 by any attachment means and is not limited to the screws. The front cover 108 has a third opening 506, having a same diameter as the opening 304 of the frame 102. In another example, the diameter of the third opening 506 is greater than the diameter of the opening 304 to allow large amount of radiations to pass through the glass window 106.

Figure 6:
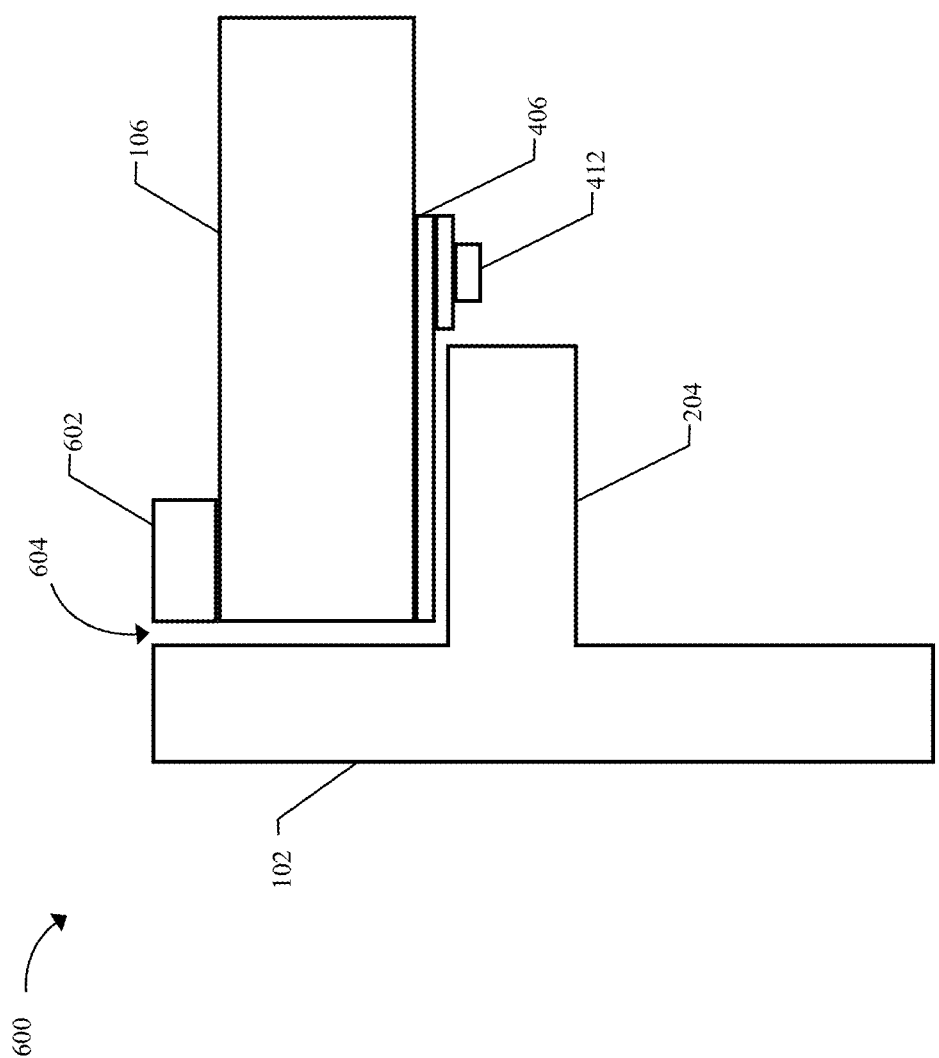
FIG. 6 illustrates a cross-sectional view of a glass window and a heater assembly of a window heating apparatus, according to one or more embodiments described herein.

FIG. 6 illustrates a sectional view 600 of the frame 102 and the glass window 106, according to one or more example embodiments described herein. The heater assembly 104, having the base 406 and the heating element 412 is placed on the ridge 204 of the frame 102. As can be seen from FIG. 6, a portion of the base 406 of the heater assembly 104 is placed over the ridge 204. The remaining portion of the base 406 that includes the heating element 412 is placed outside the ridge 204. The glass window 106 is positioned on the base 406 such that the base 406 is squeezed between the glass window 106 and the ridge 204 of the frame 102.

In an example, a support 602 of the frame 102 is disposed on the glass window 106. In an example, the support 602 may be coupled to the glass window 106 using a screw. The support 602 is provided to secure the glass window 106 to the ridge 204. A channel 604, also referred to as a flame path, is shown in FIG. 6, wherein the channel 604 is a gap between a joint formed between the glass window 106 and the frame 102 upon assembly of parts. The channel 604 is intended to arrest a flame and vent hot gases produced when an ignition of an explosive atmosphere takes place within an enclosure formed by the frame 102. Another channel may be defined between a rear side of the front cover 108 and a front side of the glass window 106. Accordingly, the window heating apparatus 100 may have other channels at different joints of parts of the window heating apparatus 100. In an example, a width of the channel 604 is in the range of about 0.26 mm to about 1 mm.

Many modifications and other embodiments of the inventions set forth herein will come to mind to one skilled in the art to which these inventions pertain having the benefit of teachings presented in the foregoing descriptions and the associated drawings. Although the figures only show certain components of the apparatus and systems described herein, it is understood that various other components may be used in conjunction with the supply management system. Therefore, it is to be understood that the inventions are not to be limited to the specific embodiments disclosed and that modifications and other embodiments are intended to be included within the scope of the appended claims. Moreover, the steps in the method described above may not necessarily occur in the order depicted in the accompanying diagrams, and in some cases one or more of the steps depicted may occur substantially simultaneously, or additional steps may be involved. Although specific terms are employed herein, they are used in a generic and descriptive sense only and not for purposes of limitation.

What is claimed is:

1. A radiation-based gas detector, comprising:
   a frame comprising:
      a support member, and
      a ridge extending radially outward from an inner surface of the frame, wherein the frame defines a groove proximal to the ridge;
   a heater assembly comprising:
      a base defining a first opening, and at least one tooth extending radially from a periphery of the first opening; and
      a printed circuit board having at least one heating element and defining a second opening, wherein the first opening and the second opening are aligned coaxially, the at least one heating element is disposed on the at least one tooth and the at least one heating element is placed outside the ridge; and
   a glass window disposed adjacent the heater assembly, wherein the glass window is coupled to the support member of the frame,
   wherein the base of the heater assembly is squeezed between the ridge of the frame and the glass window,
   wherein the groove is configured to absorb pressure applied on the glass window, and
   wherein a channel is defined between the glass window and the frame to vent gases.

2. The radiation-based gas detector of claim 1, further comprising a front cover adapted to secure the glass window and the heater assembly to the frame.

3. The radiation-based gas detector of claim 2, wherein the front cover includes a third opening, wherein the first opening, the second opening and the third opening are coaxially aligned.

4. The radiation-based gas detector of claim 1, wherein an inner edge of the at least one tooth is radially spaced from a center of the first opening.

5. The radiation-based gas detector of claim 1, further comprising at least one temperature sensor configured to determine a temperature of the glass window.

6. The radiation-based gas detector of claim 1, wherein the at least one heating element comprises a resistor.

7. The radiation-based gas detector of claim 1, wherein the groove is defined at the inner surface along an inner circumference of the frame.

8. The radiation-based gas detector of claim 7, wherein the groove is configured to absorb pressure applied on the glass window based on a compression of the groove within the predefined spacing.

9. An apparatus for detecting gas based on radiations, comprising:
   a frame comprising:
      a support member; and
      a ridge extending radially outward from an inner surface of the frame,
      wherein the frame further defines a groove proximal to the ridge;
   a heater assembly comprising:
      a base defining a first opening about a center axis of the base;
      at least one tooth extending radially from a periphery of the first opening; and
      a printed circuit board laminated on the base of the heater assembly, the printed circuit board having at least one heating element and defining a second opening, the second opening having a same diameter as the first opening, wherein the first opening and the second opening are aligned coaxially, wherein the at least one heating element is disposed on the at least one tooth and the at least one heating element is placed outside the ridge; and
   a glass window disposed on the heater assembly, wherein the glass window is in direct contact with the base of the heater assembly, wherein the glass window is coupled to the support member of the frame, wherein the base of the heater assembly is squeezed between the ridge of the frame and the glass window,
   wherein the groove is configured to absorb pressure applied on the glass window,
   wherein the heater assembly is disposed between the frame and the glass window, and
   wherein a channel is defined between the glass window and the frame to vent gases.

10. The apparatus of claim 9, further comprising a front cover, wherein a second channel is defined between a rear side of the front cover and a front side of the glass window to allow a gas to pass therethrough.

11. The apparatus of claim 10, wherein the front cover includes a third opening about a center of an axis of the front cover, wherein the first opening, the second opening, and the third opening align coaxially.

12. The apparatus of claim 10, wherein the front cover houses the glass window and the heater assembly when the front cover is secured with the frame.

13. The apparatus of claim 9, further comprising at least one temperature sensor configured to determine a temperature of the glass window.

* * * * *